United States Patent [19]

Werle et al.

[11] Patent Number: 5,723,498
[45] Date of Patent: Mar. 3, 1998

[54] COMPOSITION CAPABLE OF RELEASING ACROLEIN AND ITS USE

[75] Inventors: Peter Werle; Martin Trageser, both of Gelnhausen; Oswald Helmling; Harold Jakob, both of Hasselroth, all of Germany

[73] Assignee: Degussa Aktiengellschaft, Frankurt, Germany

[21] Appl. No.: 528,468

[22] Filed: Sep. 13, 1995

[30] Foreign Application Priority Data

Nov. 21, 1994 [DE] Germany .................. 44 41 315.7
Feb. 8, 1995 [DE] Germany .................. 195 04 042.2

[51] Int. Cl.$^6$ .................. A01N 35/02; A01N 31/14; A01N 43/24; A01N 42/28
[52] U.S. Cl. .................. 514/703; 514/23; 514/54; 514/449; 514/450; 514/452; 514/463; 514/467; 514/475; 514/698; 514/724; 514/739; 504/150; 504/154; 504/161; 568/421; 568/449; 568/465; 568/483; 568/484; 568/491; 422/36
[58] Field of Search .................. 514/703, 23, 54, 514/449, 450, 452, 463, 467, 475, 698, 724, 739; 504/150, 154, 161; 568/421, 449, 465, 483, 484, 491; 422/36; 210/748, 764

[56] References Cited

U.S. PATENT DOCUMENTS

| | | | |
|---|---|---|---|
| 3,690,857 | 9/1972 | Blair et al. | 71/66 |
| 4,851,583 | 7/1989 | Bockowski et al. | 568/465 |
| 5,079,266 | 1/1992 | Bockowski et al. | 514/703 |
| 5,183,944 | 2/1993 | Werle | 568/465 |
| 5,560,833 | 10/1996 | Werle et al. | 210/749 |

FOREIGN PATENT DOCUMENTS

| | | |
|---|---|---|
| 0 493 658 | 7/1992 | European Pat. Off. . |
| 40 38 471 | 6/1992 | Germany . |
| 43 26 575 | 2/1995 | Germany . |

*Primary Examiner*—John Pak
*Attorney, Agent, or Firm*—Beveridge, DeGrandi, Weilacher & Young, L.L.P.

[57] ABSTRACT

A composition which is capable of releasing acrolein and is easy to handle contains (i) an acetal of acrolein with a $C_{1-6}$ alcohol with 1 to 4 hydroxyl groups and (ii) an acid soluble therein and chemically compatible with a $pK_s$ value of less than 4 and (iii) is anhydrous. A preferred composition contains 2-vinyl-1,3-dioxolane as acetal, anhydrous oxalic acid, fumaric acid or maleic acid or a mixture of mono- and di($C_1$- to $C_3$-)alkyl phosphate as acid and, in addition, a non-ionic surfactant. The acrolein is released at the site of use upon contact with for example water for the purpose of combatting microbial, vegetable and animal pests.

29 Claims, No Drawings

COMPOSITION CAPABLE OF RELEASING ACROLEIN AND ITS USE

The present invention relates to a composition which is capable of releasing acrolein and exhibits a biocidal activity by releasing acrolein in the presence of water. The present invention also relates to the use of the composition for combatting microbial, vegetable and animal pests.

A large network of irrigation canals is maintained in warm climatic zones havng expansive fields and plantations under agricultural use. These canals can be readily clogged by water plants (e.g., algae and weeds). The plants hinder the rate of flow in the canals and endanger the smooth functioning of the pump stations necessary for operation. For this reason, it is customary to dope the water in such an irrigation system with a biocide.

Acrolein has proven itself in practice as a successful biocide. In addition to its as yet unexcelled activity, acrolein also offers the advantage that it degrades in water after a brief time. Thus, after a certain time acrolein is no longer effective as a biocide for irrigating fields but rather is degraded to products harmless to plant physiology. However, the handling of acrolein is very risky due to its physical and chemical properties. Acrolein is poisonous, very toxic upon inhalation, pungent, lachrymal and readily flammable (flash point −29° C., boiling point 53° C.). Furthermore, there is a potential explosive polymerization danger which can be caused by contamination of the acrolein with impurities.

In view of the risks presented, which occur both during transport and in the handling of acrolein, there is a need to perform the doping with a comparably effective biocide which is considerably less risky to handle.

U.S. Pat. No. 4,851,583 (which is incorporated by reference in its entirety, especially for its disclosure of open-chain and cyclic acetals) teaches the obtention of acrolein which is effective as pesticide by means of the deacetalation of acrolein acetals, also including cyclic acrolein acetals, in the presence of a strongly acidic ion exchanger as catalyst. However, this method is not suitable for the direct doping of flowing water because a rapid contamination or inactivation of the ion exchanger would occur. Furthermore, most acrolein acetals have only a very limited solubility in water and in addition the rate of dissolution is low. For example, approximately 10 minutes are needed to produce a solution of 2-vinyl-1,3-dioxolane (VDL), which is almost saturated under conditions of practice, in water (approximately 8% by weight) under intensive mixing. The factors cited previously make it difficult to use acrolein acetals to release acrolein at the site of utilization, that is, directly in the irrigation canals, especially since electricity for intensive mixing may not be available there.

Another way of doping water is described in U.S. Pat. No. 5,183,944 (which is incorporated by reference in its entirety, especially for its disclosure of open-chain and cyclic acetals). Here, acrolein is formed by the deacetalation of acrolein acetals in aqueous phase in the presence of a strongly acidic catalyst. For the doping of aqueous solutions the acrolein formed during the deacetalation in a reaction vessel is constantly removed from the aqueous phase and transferred into the aqueous solution to be doped. This transfer takes place either by means of a current of gas conducted through the reaction vessel, which is subsequently conducted into the aqueous solution to be doped, or by using a liquid-jet pump whose motive agent is the aqueous solution to be doped. This method is suited for doping e.g. cooling-water circuits in industrial systems but can not be used to dope the water in irrigation canals because in general neither electricity for operating the pumps nor chemically trained professional personnel is available at the doping site.

DE 43 26 575 (CA 2,129,606; U.S. patent application Ser. No. 08/280,881 filed on Jul. 27, 1994, now U.S. Pat. No. 5,560,883, which is incorporated by reference in its entirety) teaches a method of doping flowing water which avoids the disadvantages of the direct use of acrolein and is simpler to carry out than previously known methods. This method uses an acrolein acetal as biocide precursor. In this method a 25 to 95% by weight solution of an acrolein acetal in an organic solvent and a 3 to 30% by weight aqueous mineral-acid solution are placed at first in a fixed amount ratio into a mixing chamber, the reaction mixture is subsequently passed through a specially constructed deacetalation reactor and then transferred into the water to be doped.

Although the method previously evaluated represents a solution of the problem, it nevertheless has a few disadvantages: A special deacetalation reactor and, in addition to a pressure-resistant storage container for the acrolein acetal, another such container for an aqueous mineral acid are required for carrying out this method, which increases the expense; also, the regulation of the ratio between the acrolein acetal and the aqueous acid by means of perforation blending is not without problems.

SUMMARY OF THE INVENTION

The present invention provides an improved method with which microbial, vegetable and animal pests can be combatted with acrolein but without having to transport acrolein itself to the site of need and to handle it there. The method is simple to manage and is not dependent on the supply of electricity, e.g. for operating pumps, agitating and heating devices. A further problem solved is making a composition available which is reliable to use, capable of releasing acrolein, and during the use of which the preparation of a second chemical and mixing the latter into the composition at the site of use for the purpose of releasing acrolein is eliminated. Finally, the release of acrolein from the composition is carried out without the necessity of a special reactor.

The prior art problems are solved by a composition capable of releasing acrolein which is characterized (i) by a content of an acetal of acrolein with an alcohol with 1 to 6 C atoms and 1 to 4 hydroxyl groups, (ii) a content of an acid with a $pK_s$ value of less than 4 which is at least partially soluble in the acetal and therewith chemically compatible and (iii) the absence of water.

DETAILED DESCRIPTION OF THE INVENTION

It was found that such an acrolein acetal, or a mixture of such acrolein acetals, is sufficiently stable in storage in the absence of water in a mixture with one or more acids, that is, no deacetalation occurs. The composition in accordance with the present invention can therefore be transported and stored in moisture-proof barrels and does not exhibit the known handling problems of acrolein. A deacetalation of the acetal and a release of the biocidally active acrolein does not occur until the composition makes contact with water. The acid contained in the composition acts as deacetalation catalyst.

The acrolein acetals contained in accordance with the present invention in the composition are those with (i) monovalent alcohols, especially the lower alkanols such as methanol, ethanol, n- and isopropanol; (ii) bivalent alcohols, especially the lower alkylene glycols such as ethylene glycol, 1,2- and 1,3-propylene glycol; (iii) trivalent alcohols, especially glycerol, trimethylol propane and 1,2,6-hexane triol; and (iv) alcohols containing four OH groups, especially pentaerythritol. Especially preferred acrolein acetals are those with a 2-vinyl 1,3-dioxolane structure or 2-vinyl-1,3-dioxane structure, especially 2-vinyl-1,3-dioxolane and 2-vinyl-4-hydroxymethyl-1,3-dioxolane, readily obtainable from acrolein and ethylene glycol and glycerol. Acrolein acetals with longer aliphatic groups, i.e., more than 6 C atoms, are less preferred on account of their low solubility in water. In as far as the acrolein acetal still contains free hydroxyl groups, it should be checked in the individual instance whether the required chemical stability is given in the presence of the acid.

A number of requirements are placed on the acids contained in the composition. They must be soluble in sufficient amount in the acrolein acetal and be anhydrous and exhibit a $pK_s$ value of less than 4, preferably less than 3. An acid or acid mixture with a $pK_s$ value in the range of 1 to 2.5 is especially preferred. The acid and the acrolein acetal must be chemically stable in a mixture with one another in the absence of moisture—this stability is determined by an expert in the art by means of standard tests directed at determining stability in order to arrive at a composition in accordance with the invention which is stable in storage. The acid should also preferably be biologically degradable and as non-toxic as possible.

Among the monocarboxylic acids, formic acid with a $pK_s$ value of just under 4 and trihydroxybenzoic acid are effective; however, many other monocarboxylic acids, e.g. acetic acid, exhibit too low an acid strength (i.e., $pK_s$ of over 4) to make possible a sufficiently rapid hydrolysis of the acrolein acetal after the composition makes contact with water.

Some di- and polycarboxylic acids, in as far as their $pK_s$ value is below 4 and a sufficient water solubility is given, have proved to be surprisingly effective. Examples for such are: Dicarboxylic acids such as oxalic acid, maleic acid, fumaric acid, dihydroxymaleic acid and dihydroxyfumaric acid; polycarboxylic acids such as mellitic acid and pyromellitic acid. Among the dicarboxylic acids anhydrous oxalic acid and maleic acid or fumaric acid are especially preferred.

α-halogenated lower carboxylic acids such as chloro- or bromoacetic acid can also be used; fluorinated carboxylic acids are less preferred for ecological reasons.

As used herein, the term "lower" means 1–5 carbon atoms.

The following are also suitable acids:

Acidic phosphoric acid esters of lower phosphonic acids such as hydroxymethane phosphonic acid; acidic phosphonic acid esters of lower sulfonic acids such as methane sulfonic acid; and lower sulfuric acid monoalkylesters. The following are especially suitable: Phosphoric acid monoalkylester(s) or dialkylester(s) or mixtures of these esters, in which alkyl preferably stands for methyl, ethyl, n-propyl or isopropyl. Phosphoric acid mono- and/or di-alkyl esters from the reaction of phosphoric acid with an alcohol (e.g., having 1 to 3 C atoms and 1 or 2 hydroxyl groups), for example ethylene glycol or 1,3-propane diol, are also suitable.

Inorganic acids, such as $H_2SO_4$, $H_3PO_4$ as well as $HNO_3$, are not suitable on account of their chemical incompatibility with the acrolein acetals. However, other inorganic acids can be used, such as aqueous free HCl, $SO_2$, $H_3PO_3$ ($pK_s$=1.8) or $H_3AsO_4$ ($pK_s$=2.2) might be suitable.

The acrolein acetal (or acrolein acetal mixture) and the acid (or acid mixture) can be present in any desired molar ratio in the composition but the molar ratio is preferably in a range of 50 to 1 to 1 to 1, preferably 50 to 1 to 10 to 1. The higher the acid concentration in the composition is, the more rapidly the deacetalation of the acetal takes place after the addition of water. The acrolein acetal content in the composition is as high as possible in order to be able to achieve as great a biocidal activity as possible with a given amount of composition. An especially preferred composition contains a preferred acrolein acetal (or mixture of several acetals) and contains one or more of the preferred dicarboxylic acids or acid phosphoric acid esters in a weight ratio in a range of 97 to 3 to 80 to 20, especially in a range of 95 to 5 to 90 to 10.

The composition in accordance with the present invention advantageously contains one or several surfactants which are stable in the presence of the acid and of the acrolein acetal. The amount of surfactant added is customarily between 0.05 and 5% by weight relative to the composition but usually an amount between 0.2 to 1% by weight is sufficient. Especially suitable surfactants are ethoxylation products of fatty alcohols, alkyl phenols, fatty acids, fatty amides and glycerol mono- and di-fatty acid esters. Such surfactants are well known in the art. The surfactant must be sufficiently soluble in the composition and also be capable of emulsifying the composition after contact with water. In the absence of a surfactant or too low a concentration thereof a separation can occur in the case of slightly water-soluble acrolein acetals, e.g. 2-vinyl-1,3-dioxolane, so that the deacetalation takes place incompletely or in a delayed manner. In the presence of a sufficient amount of an effective surfactant the composition of the invention dissolves in a clear manner within a few seconds and the deacetalation also takes place practically quantitatively at approximately 20° C. within a few minutes.

An especially advantageous composition consists essentially of 80 to 97% by weight 2-vinyl 1,3-dioxolane, 2 to 20% by weight dicarboxylic acid from the series of anhydrous oxalic acid, maleic acid and fumaric acid, especially anhydrous oxalic acid or phosphoric acid mono- and/or -di($C_1$- to $C_3$)alkylester, and 0.1 to 5% by weight, preferably 0.2 to 1% by weight, of a non-ionic surfactant based on an ethoxylation product of the previously named classes of substances; it is especially preferable if the composition contains a polyoxyethylene adduct of a glycerol monofatty acid ester as surfactant.

In addition to the components essential for the invention, and the surfactant which is preferably also present in addition, the composition can contain other additives in as far as they are stable in the composition. Possible other additives are e.g. other biocides and water-soluble organic solvents such as lower alcohols.

The compositions of the invention can be produced by simply mixing the components together and are in general clear solutions. The compatibility of the components with each other is assured beforehand by conventional storage tests.

The composition of the invention can be used, since the highly effective biocide acrolein is released upon contact with water, as a means for combatting microbial, vegetable and animal pests. The pests include in particular bacteria and fungi, algae and water weeds, insects, worms and rodents.

In order to combat microbial, vegetable and animal pests with acrolein, a composition in accordance with the present invention is either (i) brought into direct contact with a moist medium (e.g., terrestrial) containing the pests to be combatted or (ii) mixed with water in a weight ratio of 1:1 to 1:50 and the reaction mixture added directly or after further dilution with water into the medium (e.g., aquatic) containing the pests to be combatted after a reaction time which is necessary for an extensive deacetalation of the acrolein acetal contained in the composition.

The ratio of acrolein acetal to water in method alternative (ii) is advantageously in such a range that during the deacetalation a pH of around/below 2 is maintained for a few minutes. In general, the ratio is between 1 to 1 and 1 to 50, preferably between 1 to 5 and 1 to 20.

For the purpose of a rapid dissolution of the composition in water the composition is preferably sprayed into water with a single, or better yet, multiple spray jet so that very fine and therefore readily emulsifiable and rapidly soluble droplets result immediately. The spraying in can be effected e.g. using appropriate jets (nozzles) and a bottle of compressed gas.

In method alternative (i) acrolein is released to the moisture content of the medium in a correspondingly slower manner. Method alternative (i) can be used e.g. to combat nematodes or rodents in the ground.

Alternative (ii) is especially suited for combating aquatic pests such as e.g. algae and weeds in irrigation canals. For this, the deacetalated mixture is introduced continuously or periodically in such an amount into the water containing the pests that an acrolein content in a range of 0.1 to 20 ppm acrolein is maintained in it.

Advantages of the composition of the invention are its easy production, good storage capacity and ability to be handled and its ability to be directly used to combat pests. Since the composition itself contains the deacetalation catalyst, such a catalyst does not have to be mixed in dosed form into the composition containing acrolein acetal at the site of use. Due to the selected components of the composition, neither an expensive device nor a special deacetalation reactor are necessary for being able to release acrolein from the acrolein acetal. The method for combatting bacterial, vegetable and animal pests thus turns out to be simple, requires no electricity and can be carried out by personnel with little training.

EXAMPLE 1

Manufacture of the composition and release of acrolein.

95 g 2-vinyl-1,3-dioxolane (VDL), 5 g of a 60:40 weight mixture of monoisopropyl- and diisopropyl phosphoric acid ester as well as 1 g surfactant based on polyoxyethylene glycerol monooleate (Tegotens® 02 of the The. Goldschmidt AG) are mixed. The composition is a clear solution.

The composition obtained in this manner is sprayed into 1000 ml water with a spray jet with a pressure from a bottle of $N_2$ compressed gas of 3 bar. The emulsion which is formed at first becomes a clear solution in a few seconds. After 10 minutes dwell time 99.6% of the acrolein bound in the VDL has been released (determination by gas chromatography).

As a result of the addition of the aqueous concentrate containing released acrolein to water containing aquatic pests in a ratio of e.g. 1 to 5000, an acrolein concentration of approximately 10.6 ppm is adjusted, which is suitable for combatting the pests.

EXAMPLE 2

25 g anhydrous oxalic acid are added under agitation to a mixture of 470.2 g VDL and 4.7 g surfactant in accordance with example 1 (Tegotens® 02). After approximately 10 min a practically colorless, homogeneous solution is obtained. This "L" solution is stable in storage.

Investigation of the release of acrolein: The "L" solution is charged into water in the volume ratio indicated in the following table; the mixture is agitated, at which time hydrolysis takes place and acrolein is released. The reaction is stopped by the addition of sodium hydroxide solution (final pH: 6–7); the formed acrolein and ethylene glycol as well as the residual VDL content are measured with gas chromatography. A conversion of the VDL in accordance with the table takes place.

| Volume ratio "L" to water | Conversion of VDL (hydrolysis rate) in % after | | |
|---|---|---|---|
| | 2 min | 4 min | 8 min |
| 1:5 | 85.9 | 98.6 | 99.5 |
| 1:10 | 91.0 | 99.2 | 99.7 |
| 1:20 | 71.7 | 92.9 | 99.6 |

EXAMPLE 3

10 g anhydrous maleic acid are dissolved under agitation at 35° C. in a mixture of 188.2 g VDL and 0.9 g surfactant in accordance with example 1 (Tegotens® 02). 10 ml of this solution are charged into 60 ml water; the mixture is agitated 6 min, the reaction stopped with NaOH and the residual content of non-hydrolysed VDL determined. A conversion of 98.2% results.

EXAMPLE 4

Method of preventing flowing water from becoming clogged with algae and weeds.

A composition in accordance with the invention is brought to the site of application in a container sealed against moisture and provided with a feed tube. The composition exiting from the feed tube is conducted via a pressure-resistant hose into the water to be doped by applying a pressure of 3 bar from a bottle of $N_2$ compressed gas onto the container. A jet is located at the end of this hose which jet makes it possible to obtain a fine distribution of the composition in an amount of the water to be doped which is at first limited. In order to obtain the conditions of time and acidity necessary for splitting the acetal the developing solution is only diluted at first to the extent that a pH of approximately 1.5 to 2 is maintained for a time of about 5 to 10 minutes. After sufficient deacetalation the deacetalized, aqueous concentrate containing the acrolein is diluted with an amount of the water to be doped which is sufficient for arriving at the desired application concentration.

A suitable measure for maintaining optimal deacetalation conditions is to spray into a container filled with a defined amount of water; this container is itself purposefully located in the water to be doped. After expiration of the dwell time the container is opened and the released acrolein washed into the canal. Alternatively, the spraying can be into a tube (or hose) through which water flows, which is located in the water to be doped, which lets only a limited amount of water pass through as a consequence of its length and cross section at the given rate of flow and assures a sufficient dwell time prior to further diluting.

EXAMPLE 5

German Application 195 05 171.8, filed on 16 Feb. 1995, and U.S. patent application Ser. No. 08/476,128, filed on 7 Jun. 1995, are relied on and incorporated by reference in their entirety.

Acroleindimethylacetal (ADMA)—To a mixture of 95 g ADMA and 0.5 g Tensid (Tegotens® 02) there was dissolved with stirring 5 g maleic acid anhydride. This solution was introduced into 600 ml of water. The barely soluble acetyl is quickly emulsified with a formation of a milky opaque emulsion. After 10 minutes the solution was clear and homogeneous. After stopping the reaction, there was found 0.5% ADMA which means that the degree of conversion was 99.5%.

Vinyldioxan—In a mixture of 142.5 g 2-vinyldioxan and 1.0 g of an emulsifier based on nonyl phenol ethoxylate there was dissolved 7.5 g of maleic acid anhydride. The clear solution was stirred into 900 ml water. The vinyldioxan was emulsified and gradually dissolved and after 10 to 15 minutes was completely hydrolyzed. The solution was also clear and colorless and smelled strongly of acrolein. The conversion was found to be 99.2% by gas chromatography.

Maleic acid anhydride hydrolyzes to maleic acid and operates as a deacetalization catalyst.

Further variations and modifications of the foregoing will be apparent to those skilled in the art and such variations and modifications are intended to be encompassed by the claims that are appended hereto.

German Priority Application 195 04 042.2, filed on 8 Feb. 1995, and 44 41 315.7, filed on 21 Nov. 1994, are relied on and incorporated by reference in their entirety.

We claim:

1. A storage stable, transportable composition capable of releasing acrolein, comprising (i) at least one acetal of acrolein with an alcohol with 1 to 6 C atoms and 1 to 4 hydroxyl groups, and (ii) at least one acid with a $pK_s$ value of less than 4 which is at least partially soluble in said acetal and chemically compatible therewith and which is a member selected from the group consisting of a monocarboxylic acid and a polycarboxylic acid, wherein said composition contains no water.

2. The composition according to claim 1, wherein said acetal is 2-vinyl-1,3-dioxolane or 2-vinyl-4-hydroxymethyl-1,3-dioxolane.

3. The composition according to claim 1, wherein said alcohol is selected from the group consisting of monovalent alcohol, bivalent alcohol, trivalent alcohol and polyvalent alcohol.

4. The composition according to claim 3, wherein said monovalent alcohol is methanol, ethanol, n-propanol or isopropanol, said bivalent alcohol is ethylene glycol, 1,2-propylene glycol or 1,3-propylene glycol, said trivalent alcohol is glycerol, trimethylol propane or 1,2,6-hexane triol, and said polyvalent alcohol is pentaerythritol.

5. The composition according to claim 4, wherein said $pK_s$ value is less than 3.

6. The composition according to claim 5, wherein said $pK_s$ value is between 1 and 2.5.

7. The composition according to claim 1, wherein said monocarboxylic acid is formic acid or trihydroxybenzoic acid.

8. The composition according to claim 1, wherein said polycarboxylic acid is a dicarboxylic acid.

9. The composition according to claim 8, wherein said dicarboxylic acid is selected from the group consisting of oxalic acid, maleic acid, fumaric acid, dihydroxymaleic and dihydroxyfumaric acid.

10. The composition according to claim 8, wherein said dicarboxylic acid is selected from the group consisting of anhydrous oxalic acid, anhydrous maleic acid, and anhydrous fumaric acid.

11. The composition according to claim 1, wherein said polycarboxylic acid is mellitic acid or pyromellitic acid.

12. The composition according to claim 1, wherein said monocarboxylic acid is an α-halogenated lower carboxylic acid.

13. The composition according to claim 12, wherein said α-halogenated lower carboxylic acid is chloroacetic or bromoacetic acid.

14. The composition according to claim 1, wherein said composition contains said acetal and said acid in a molar ratio of 50:1 to 1:1.

15. The composition according to claim 1, wherein said composition contains said acetal and said acid in a weight ratio in a range of 97:3 to 80:20.

16. The composition according to claim 15, wherein said composition contains said acetal and said acid in a weight ratio in a range of 95:5 to 90:10.

17. The composition according to claim 1, further comprising between 0.05 and 5% by weight of a surfactant.

18. The composition according to claim 17, comprising between 0.2 and 1% by weight of a surfactant.

19. The composition according to claim 17, wherein said surfactant is an ethoxylation product of a fatty alcohol, a alkyl phenol, a fatty acid, a fatty amide, a glycerol monofatty acid ester, or a glycerol difatty acid ester.

20. The composition according to claim 1, wherein said composition consists essentially of 80 to 97% by weight 2-vinyl 1,3-dioxolane, 2 to 20% by weight of acid selected from the group consisting of anhydrous oxalic acid, anhydrous maleic acid, anhydrous fumaric acid, phosphoric acid mono($C_{1-3}$)alkylester, and phosphoric acid di($C_{1-3}$) alkylester, and 0.1 to 5% by weight of a surfactant.

21. The composition according to claim 20, wherein said surfactant is a polyoxyethylene adduct of a glycerol monofatty acid ester.

22. A method of combating microbial, vegetable and animal pests contained in a moist medium with acrolein, comprising (i) bringing a storage stable composition capable of releasing acrolein into direct contact with a moist medium containing said pests or (ii) mixing said composition with water in a weight ratio of 1:1 to 1:50 to form a reaction mixture and adding said reaction mixture directly, or optionally after further dilution with water, into the moist medium containing said pests after a reaction time which is necessary for an extensive deacetalation of the acrolein acetal contained in said composition and thereby releasing acrolein in said medium, said composition comprising (i) at least one acetal of acrolein with an alcohol with 1 to 6 C atoms and 1 to 4 hydroxyl groups, and (ii) at least one acid with a $pK_s$ value of less than 4 which is at least partially soluble in said acetal and chemically compatible therewith and which is a member selected from the group consisting of a monocarboxylic acid and a polycarboxylic acid, wherein said composition contains no water.

23. The method according to claim 22, wherein said weight ratio is 1:5 to 1:20.

24. The method according to claim 22, wherein said reaction mixture is introduced continuously or periodically into said moist medium in an amount effective to maintain an acrolein content in a range of 0.1 to 20 ppm acrolein in said moist medium.

25. A kit for combating microbial, vegetable and animal pests with acrolein, comprising a container containing a mixture of (i) at least one acetal of acrolein with an alcohol with 1 to 6 C atoms and 1 to 4 hydroxyl groups, and (ii) at least one acid with a $pK_s$ value of less than 4 which is at least partially soluble in said acetal and chemically compatible therewith and which is a member selected from the group consisting of a monocarboxylic acid and a polycarboxylic acid, wherein said mixture contains no water.

26. A method of combating microbial, vegetable and animal pests in an irrigation canal with acrolein comprising (i) bringing a storage stable composition capable of releasing acrolein into direct contact with said irrigation canal containing said pests or (ii) mixing said composition with water in a weight ratio of 1:1 to 1:50 to form a reaction mixture and adding said reaction mixture directly, or optionally after further dilution with water, into said irrigation canal containing said pests after a reaction time which is necessary for an extensive deacetalation of the acrolein acetal contained in said composition and thereby releasing acrolein into said irrigation canal, said composition comprising (i) at least one acetal of acrolein with an alcohol with 1 to 6 C atoms and 1 to 4 hydroxyl groups, and (ii) at least one acid with a $pK_s$ value of less than 4 which is at least partially soluble in said acetal and chemically compatible therewith and which is a member selected from the group consisting of a monocarboxylic acid and a polycarboxylic acid, wherein said composition contains no water.

27. A method of combating microbial, vegetable and animal pests in an irrigation canal with acrolein consisting essentially of (i) bringing a storage stable composition capable of releasing acrolein into direct contact with said irrigation canal containing said pests or (ii) mixing said composition with water in a weight ratio of 1:1 to 1:50 to form a reaction mixture and adding said reaction mixture directly, or optionally after further dilution with water, into said irrigation canal containing said pests after a reaction time which is necessary for an extensive deacetalation of the acrolein acetal contained in said composition and thereby releasing acrolein into said irrigation canal, said composition comprising (i) at least one acetal of acrolein with an alcohol with 1 to 6 C atoms and 1 to 4 hydroxyl groups, and (ii) at least one acid with a $pK_s$ value of less than 4 which is at least partially soluble in said acetal and chemically compatible therewith and which is a member selected from the group consisting of a monocarboxylic acid and a polycarboxylic acid, wherein said composition contains no water.

28. A method of combating microbial or vegetable pests contained in an irrigation canal with acrolein comprising transporting a moisture proof barrel containing a storage stable composition to the site of an irrigation canal and introducing the contents of said moisture proof barrel into said irrigation canal, or mixing the contents of said moisture proof barrel with water in a weight ratio of 1:1 to 1:50 to form a reaction mixture and adding said reaction mixture directly, or optionally after further dilution with water, into the irrigation canal containing said pests after a reaction time which is necessary for an extensive deacetalation of the acrolein acetal contained in said composition and thereby releasing acrolein into said irrigation canal, said composition comprising (i) at least one acetal of acrolein with an alcohol with 1 to 6 C atoms and 1 to 4 hydroxyl groups, and (ii) at least one acid with a $pK_s$ value of less than 4 which is at least partially soluble in said acetal and chemically compatible therewith and which is a member selected from the group consisting of a monocarboxylic acid and a polycarboxylic acid, wherein said composition contains no water.

29. A moisture proof container containing the composition according to claim 1.

* * * * *